United States Patent [19]

Walker

[11] 4,139,742
[45] Feb. 13, 1979

[54] CUTANEOUS COMMUNICATION DEVICE

[76] Inventor: Jay F. Walker, P.O. Box 2012, Newport Beach, Calif. 92663

[21] Appl. No.: 764,879

[22] Filed: Feb. 2, 1977

[51] Int. Cl.² ............................................. H04R 25/00
[52] U.S. Cl. ................................................ 179/107 BC
[58] Field of Search ............ 179/107 BC, 114 R, 120; 340/407

[56] References Cited

U.S. PATENT DOCUMENTS

| 1,655,283 | 1/1928 | Morton | 179/120 |
| 2,150,364 | 3/1939 | Dudley | 179/107 BC |
| 2,233,848 | 3/1941 | Polk | 179/107 BC |
| 2,582,277 | 1/1952 | Powlison | 340/407 |

FOREIGN PATENT DOCUMENTS

| 1231085 | 9/1960 | France | 179/107 BC |
| 212533 | 11/1940 | Switzerland | 179/114 R |
| 253511 | 3/1948 | Switzerland | 179/114 R |

OTHER PUBLICATIONS

Research Reviews, Oct. 1954, "Hearing Through the Skin", F. A. Geldard, (Pages Unknown).

Primary Examiner—George G. Stellar
Attorney, Agent, or Firm—Sherman & Shalloway

[57] ABSTRACT

An apparatus for communication by transmitting voice signals to cutaneous nerve receptors, includes a transducer for stimulating the receptors, an amplifier for driving the transducer and a microphone for applying voice signals to the amplifier. By utilizing this apparatus, the hearing structure of the ear can be partially or wholly bypassed, thus providing another communication channel which can be used, for example, to help the deaf to communicate and to communicate when "noise" interferes with normal "hearing".

8 Claims, 4 Drawing Figures

CUTANEOUS COMMUNICATION DEVICE

BACKGROUND OF THE INVENTION

1. Field of the Invention

This invention relates to an apparatus for transmitting signals, such as voice signals, to a person. More particularly, this invention relates to an apparatus which transmits audio signals to cutaneous nerve receptors in such a way that these receptors transmit intelligible signals to the brain.

2. Technical Considerations and Prior Art

Until relatively recently, it has been generally thought that a person can "hear" audio frequency vibrations only with his ears and that it is necessary to utilize the ear structure for effective communication. It has also been known that the body has cutaneous nerve receptors which sense mechanical vibrations in the air and transmit those vibrations to the brain, bypassing the ear structure. To date, there have been attempts to utilize these cutaneous nerve receptors to help partially and wholly deaf people and people with speech defects to both speak and speak more clearly. However, no attempt has been made to utilize the cutaneous nerve receptors as a primary vehicle for transmitting speech.

There are many situations in which it is difficult or undesirable to communicate verbally by transmitting messages through the ear. For example, it is extremely difficult to communicate audibly in industrial plants where ear muffs are worn. In addition, motorcycle riders and their passengers have difficulty talking to one another because of noise generated by both the motorcycle engine and wind. Furthermore, there may be situations in which a person needs to receive both audio communication and cutaneous communication. For example, spoken messages can be received by a radio receiver and transmitted cutaneously to the brain while a person is otherwise occupied or otherwise communicating verbally. Such a device could have use in a "Bell Boy" call director type of communications system.

It has been found that many people who are partially deaf are afflicted with sound distortion, so that even if they hear a particular sound or word, the word becomes so distorted by the inner ear that it is indecipherable. Accordingly, if such a deaf person can be trained to bypass the inner ear in order to "hear", this distortion may be eliminated.

OBJECTS OF THE INVENTION

In view of these and other considerations, it is an object of the invention to provide a new and improved apparatus for communication wherein the apparatus utilizes cutaneous nerve receptors to transmit audio signals through the skin to the brain.

It is an additional object of the instant invention to provide a new and improved apparatus for communication wherein the ear is partially or wholly bypassed when transmitting audio signals to the brain.

It is still a further object of the instant invention to provide a new and improved system for communication wherein audio communication is still possible when circumstances prevent utilizing the ear.

It is still another object of the instant invention to provide a new and improved apparatus for communication wherein the apparatus is readily portable and can be carried on one's person while concealed.

It is another object of the instant invention to provide a new and improved apparatus for audio communication wherein the apparatus utilizes an amplifier to convert sound waves into localized tactile impulses which are transmitted by cutaneous nerves to the brain.

SUMMARY OF THE INVENTION

With these and other objects in mind, the instant invention contemplates a readily portable communication system for transmitting audio signals to a person. The system includes a microphone for converting audio frequencies into electrical signals and an amplifier for converting the electrical signals into signals for driving a mechanical oscillator. The mechanical oscillator is mounted in a casing which is attached to the wrist of the person being communicated with and transmits vibration to cutaneous nerve receptors which, in turn, relay the vibrations to the person's brain. Since the vibrations are a direct analogue of spoken words, they contain intelligence which, it has been found, can be readily understood by the brain.

DETAILED DESCRIPTION

Figure 1:
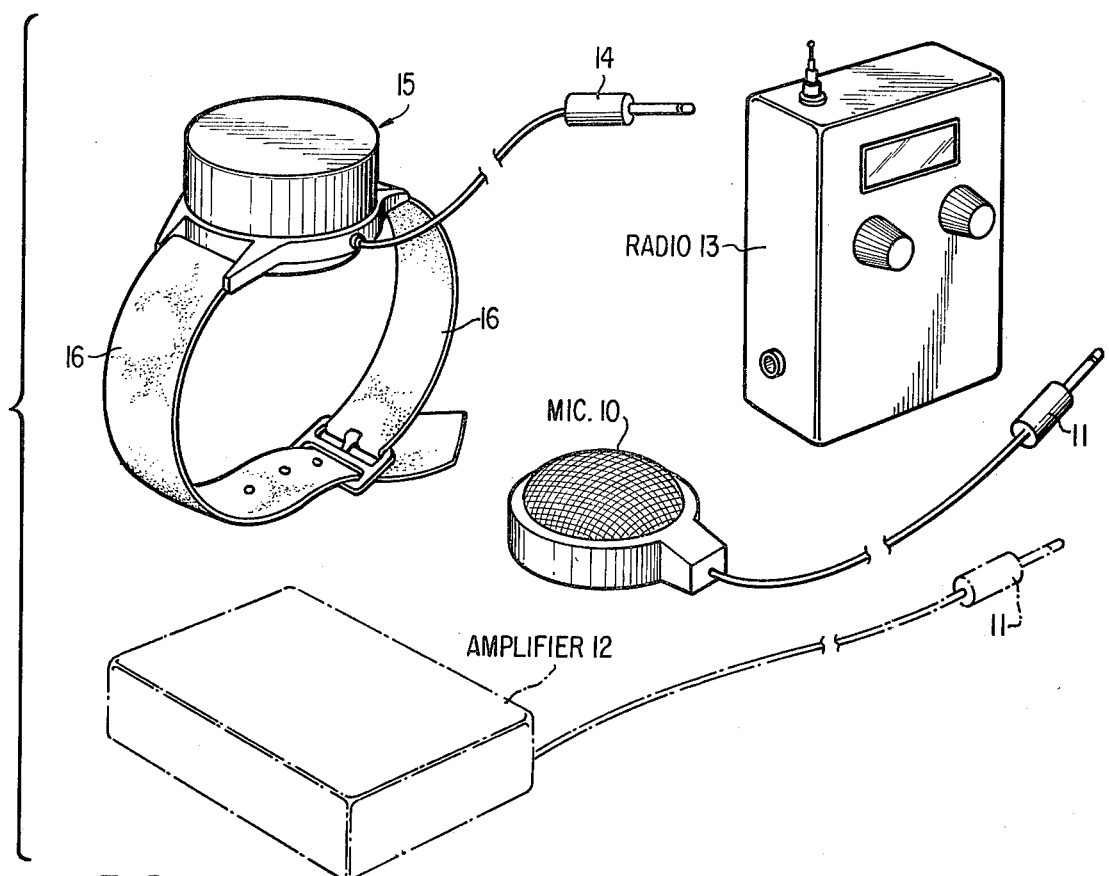
FIG. 1 is a perspective view showing a transducer, amplifier, microphone and radio receiver which comprise the instant invention.

Referring now to FIG. 1, the various parts of the apparatus according to the instant invention are shown in an exploded view. Essentially, the apparatus consists of a conventional microphone 10 which is connected by a jack 11 to an audio frequency amplifier 12. Optionally, instead of using the microphone 10, a radio receiver 13 may be connected by a jack 11 to the audio frequency amplifier 12. In either case, the purpose is to apply audio frequency signals, such as voice signals, to the amplifier 12. The microphone 10 is of a conventional design and is preferably small enough to be mounted on a person's coat pocket, tie or lapel.

The audio amplifier 12 is connected via a jack 14 to drive a mechanical transducer 15. The mechanical transducer 15 is approximately the size of a wrist watch and is mounted on a person's wrist with straps 16. The transducer 15 includes a plunger 20 which projects out of the bottom thereof and engages the skin. When vibrated the plunger 20 transmits mechanical vibrations to the cutaneous nerve receptors just beneath the outer surface of the skin. Since the mechanical transducer 15 is driven by the audio amplifier 12, the plunger 20 has a mechanical vibration pattern which follows the electrical output of the amplifier. Since the input to the amplifier 12 is in the form of voice signals, the electrical output of the amplifier is analogous to voice signals thereby causing the transducer 15 to move to the plunger 20 in a vibrational pattern analogous to voice signals.

The cutaneous nerve receptors are, of course, continually receiving audio frequency vibrations from the surrounding atmosphere and from objects in engagement with the skin, however these signals are not localized and are of relatively low power. In addition, there is no mechanism in the cutaneous nerve receptor system for discriminating between voice signals and the impingement of a myriad of other signals on the skin. Consequently, the brain cannot ordinarily use the cutaneous nerve receptor system as an input for signals which originated as speech. This invention allows the brain to utilize these speech signals because the microphone 10 helps to isolate audible voice signals from other signals, while the amplifier 12 increases the power of the voice signals and the plunger 20 of the transducer 15 localizes the signals to a small area of the skin. The cutaneous nerve receptors of the wrist tend to be highly developed and sensitive due to their proximity to hand. Accordingly, it has been found that straping the transducer 15 to the wrist affords an ideal means for attaching the transducer to the body.

Figure 2:
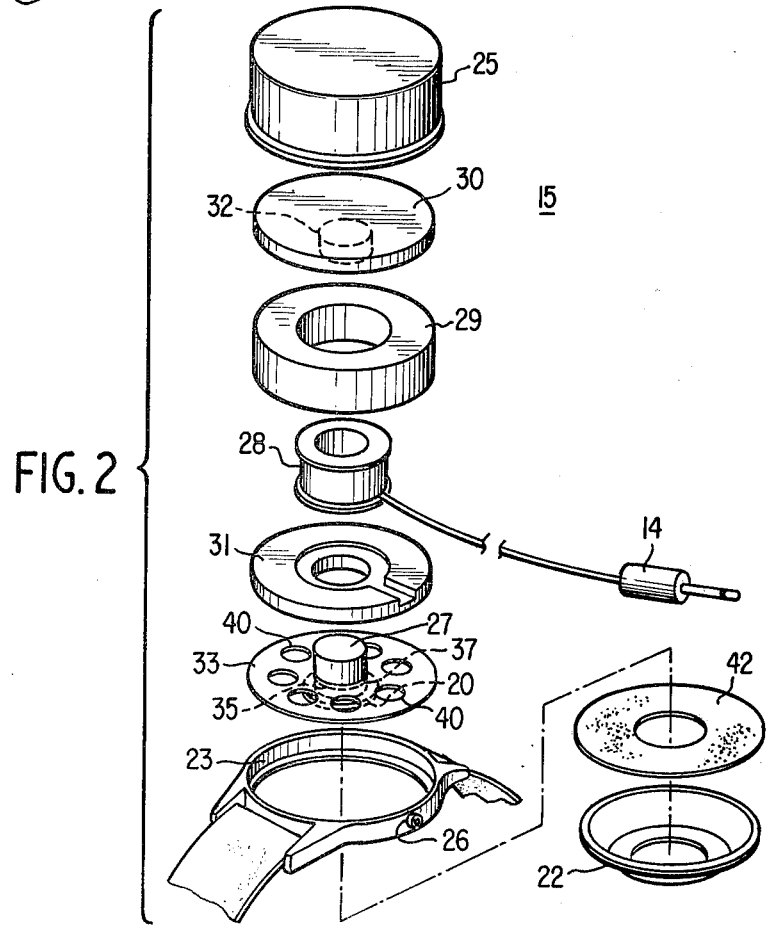
FIG. 2 is an exploded view in perspective of the transducer of the instant invention.

Referring now to FIG. 2, the transducer 15 includes a bottom assembly cover 22 made preferably of stainless steel or chromeplated non-magnetic steel which is attached to a non-magnetic annular assembly ring 23 that also retains a top assembly cover 25. The top assembly cover is made of a non-magnetic material such as duraluminum, plastic or the like. The annular assembly ring 23 mounts the straps 16 and has an opening 26 therethrough for the lead from the jack 14. The plunger 20 is attached to a cylindrical soft iron armature 27 which is driven by an electromagnet arrangement which includes a coil 28 mounted within an annular permanent magnet 29. A soft iron top pole 30 fits over the top of the magnet 29 while a soft iron bottom pole 31 fits over the bottom of the magnet. The coil 28 is retained within the annulus of the magnet and armature 27 of the plunger 20 projects into the coil. The top pole 30 has a projection 32 which projects down into the coil 28 while the armature 27 is held in spaced relation to the projection 32 by a berrilium copper flange 33.

Figure 3:
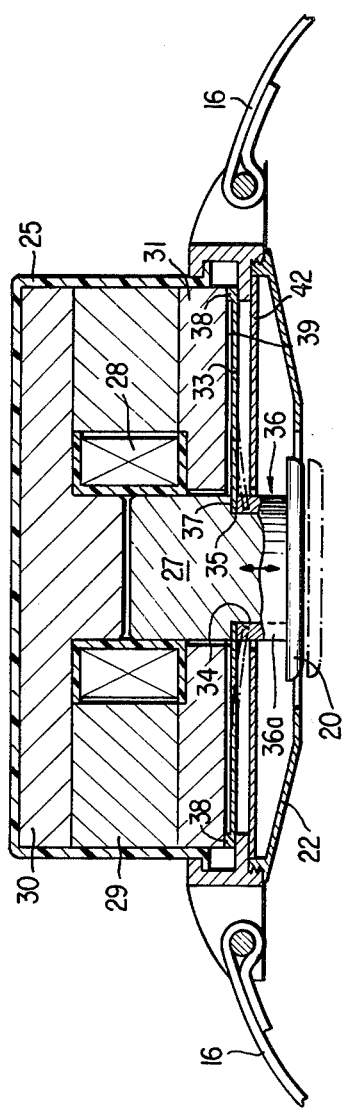
FIG. 3 is a side view of a cross section of the assembled magnet shown in FIG. 2.

As is seen in FIG. 2 & 3 the armature 27 has a reduced diameter projection 34 which projects through a central opening 35 in the beryllium copper flange 33. An aluminum cap 36 having a hollow shank 36a and a diameter greater than the opening 35 is welded to the projection 34 forming a circular slot 37 which receives the edge of the berrilium copper flange 33. Preferably the slot 37 is slightly wider than the thickness of the flange 33 so that the plunger assembly 20 does not bind with the edges of the opening 35.

The berrilium copper flange 33 has a thickness of approximately 0.004 inch, is resilient and serves as a flexible support for the plunger assembly which normally keeps the armature 27 spaced from the projection 32. When the coil 28 is energized the armature 27 is attracted by the top pole 30 against the bias of the flange 33. Preferably, the flange 33 is welded or otherwise secured on annular shoulder 38 which holds the flange in spaced relation with the bottom surface 39 of the bottom pole 31 thereby allowing the flange 33 to flex. Proper resiliency of the flange 33 is obtained by a ring of uniformly spaced holes 40 punched through the flange.

In order to prevent moisture damage and to block transmission of vibrations to the bottom cover 22, an annular moisture barrier 42 fits around the shank 36a of the cap 36.

It has been found that movement or excursion of the plunger from 0 to 40 thousandths of an inch provides the proper amplitude for stimulation of the cutaneous nerve receptors. This amplitude is supplied at frequencies of 30 to 1,000 Hz depending on the signals received from the audio amplifier 12. The coil 28 is of 30 gauge wire having 450 turns and the magnet is ceramic having a field intensity of 650 gauss. The transducer can, however, operate efficiently with a magnet having an intensity in the range of 500 to 1,500 gauss.

Figure 4:
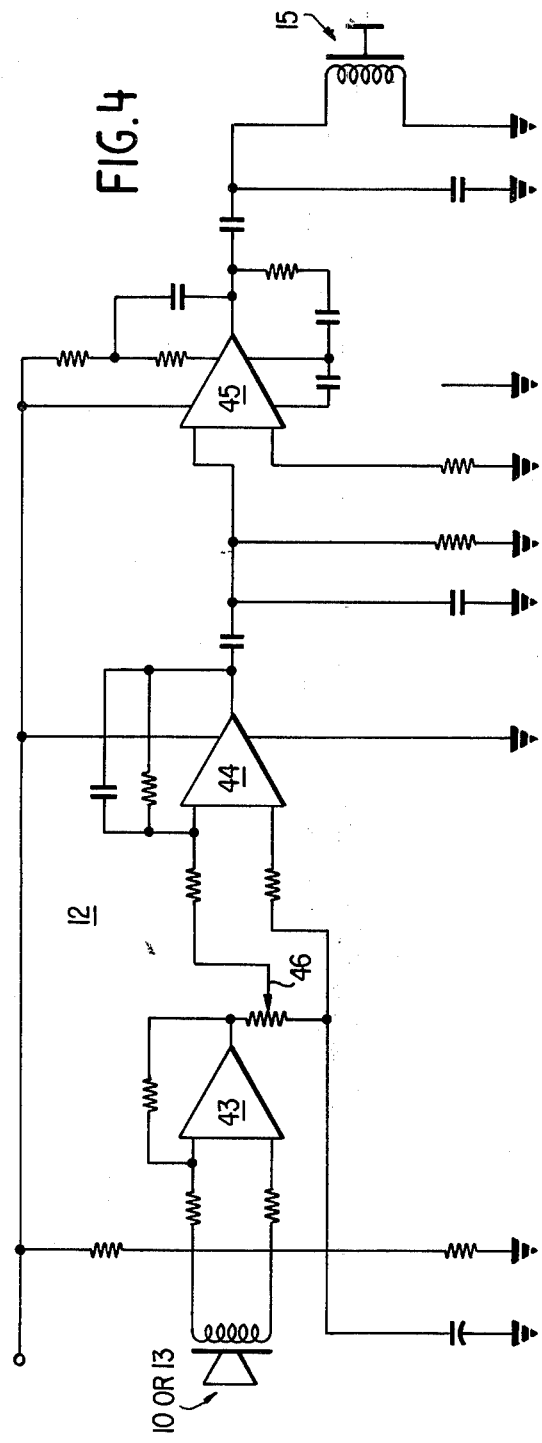
FIG. 4 is a circuit diagram of the circuitry utilized in the audio amplifier of FIG. 1.

Referring now to FIG. 4, there is shown a circuit diagram of the various components which are used in the audio amplifier 12. Preferably, the audio amplifier 12 has an output range of 0 to 1.5 watts which is applied through the jack 14 to the transducer 15. The audio amplifier 12 is powered by a low voltage battery e.g. 1 to 12 volts preferably a 8 or 9 volt battery and, therefore, is quite compact and may be carried in one's pocket or strapped to one's body. The amplifier 12 includes three cascaded stages 43, 44 and 45 which are connected with various R-C networks to filter the incoming signal so that the signal applied to the transducer 15 is analogous to the voice signal received by the microphone 10 or radio receiver 13. Consequently, the output vibrations from the transducer 15 are analogous in frequency and amplitude to voice signals impressed upon the microphone 10 or received by the radio receiver 13. The output of power of the amplifier 12 is controlled by a potentiometer 46 disposed between the stages 43 and 44.

As the plunger 20 is oscillated by the transducer 15 there is an acoustical transmission of vibrations to the brain via the blood within the venial system of the body, as well as neurological transmission due to mechanical stimulation of neurons.

The aforedescribed apparatus enables the user to "hear" speech through his skin as opposed to the conventional method of hearing with the ear. Consequently, in many situations where the ear cannot be used either because the ear is damaged or because there is too much surrounding noise this apparatus provides an alternative approach.

The foregoing description is merely illustrative of the invention, which would be limited only by the following appended claims.

What is claimed is:

1. A portable communication apparatus for transmitting audio signals to a person comprising:
   a microphone for converting audio frequencies into electrical signals;
   an amplifier for converting the electrical signals into signals for driving;
   an electro-magnet having a top pole and a bottom annular pole which retain an annular permanent magnet therebetween wherein a coil is positioned within the permanent magnet;
   a plunger having an armature which projects into the coil and a head which engages the skin, said plunger having an excursion ratio in the range of 0–0.04 inches and a vibrational frequency of 30 to 1,000 Hz; and
   a resilient flange for supporting the plunger on the bottom pole with the armature in space relation to the top pole wherein the electro-magnet is mounted in a casing which is attached to the wrist of the person and transmits audio signals to cutaneous nerve receptors in the wrist which, in turn, relay reception of the audio signals to the persons brain.

2. The apparatus of claim 1 wherein the audio amplifier is powered by a low voltage D.C. battery and has an output to 0–1.5 watts.

3. The apparatus of claim 1 wherein the resilient flange is annular and is supported in spaced relation to the surface of the bottom pole by an annular shoulder on the bottom pole to which the flange is attached.

4. The apparatus of claim 1 wherein the top flange includes a projection with projects into the coil, and wherein the resilient flange holds the armature in spaced relation to the projection and in spaced relation to the bottom pole.

5. The apparatus of claim 4 wherein the resilient flange is annular and is supported in spaced relation to the surface of the bottom pole by an annular shoulder on the bottom pole to which the flange is attached.

6. The apparatus of claim 5 wherein the flange has an annular ring of uniformly spaced holes therein surrounding the plunger.

7. The apparatus of claim 6 wherein the flange is made of berrilium copper.

8. The apparatus of claim 7 wherein the flange is 0.004 inches thick.

* * * * *